US010156504B2

(12) United States Patent
Brüchig et al.

(10) Patent No.: US 10,156,504 B2
(45) Date of Patent: *Dec. 18, 2018

(54) APPARATUS FOR OPTICAL IN-SITU GAS ANALYSIS

(71) Applicant: SICK AG, Waldkirch (DE)

(72) Inventors: Florian Brüchig, Waldkirch (DE); Ingo Schiffler, Waldkirch (DE); Jürgen Kaufmann, Waldkirch (DE)

(73) Assignee: SICK AG, Waldkirch (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/484,164

(22) Filed: Apr. 11, 2017

(65) Prior Publication Data

US 2017/0299484 A1   Oct. 19, 2017

(30) Foreign Application Priority Data

Apr. 15, 2016 (EP) ..................... 16165648

(51) Int. Cl.
   *G01N 1/40*      (2006.01)
   *G01N 21/31*     (2006.01)
   (Continued)

(52) U.S. Cl.
   CPC ............ *G01N 1/4077* (2013.01); *F16K 7/07* (2013.01); *G01N 1/2205* (2013.01);
   (Continued)

(58) Field of Classification Search
   CPC ......... G01N 1/4077; G01N 2001/4088; G01N 21/31; G01N 33/0044; G01N 21/031
   See application file for complete search history.

(56) References Cited

U.S. PATENT DOCUMENTS

| 4,549,080 A | 10/1985 | Baskins et al. |
| 2005/0011968 A1* | 1/2005 | Tracey ................. B05B 7/0408 239/195 |
| 2007/0187529 A1* | 8/2007 | Tracey ................. B05B 7/0408 239/196 |

FOREIGN PATENT DOCUMENTS

| DE | 19704960 A1 | 8/1998 | |
| DE | 102008044171 A1 * | 6/2010 | ........... G01N 21/031 |
| DE | 102014002087 A1 | 8/2015 | |

OTHER PUBLICATIONS

European Search Report dated Sep. 5, 2016 in corresponding European Application No. 16165648.3.

(Continued)

*Primary Examiner* — Violeta A Prieto
(74) *Attorney, Agent, or Firm* — Nath, Goldberg & Meyer; Jerald L. Meyer; Stanley N. Protigal

(57) ABSTRACT

An apparatus for optical in-situ gas analysis includes: a housing; a measuring lance a first end connected to the housing and a second end projecting into the gas to be measured; a light transmitter that is arranged in the housing and whose light is conducted into the measuring lance and is reflected by a reflector arranged at the second end onto a light receiver, and the optical path defines an optical measurement path within the measuring lance; and, an evaluation device for evaluating received light signals of the light receiver. In order to be able to reduce the consumption of test gas, the measuring lance has an outer tube, with the outer tube having openings for the gas to be measured. The openings can be closed by at least one seal for the test phase, with the seal searingly closing the openings by the enlargement of its volume.

4 Claims, 4 Drawing Sheets

Figure 1:
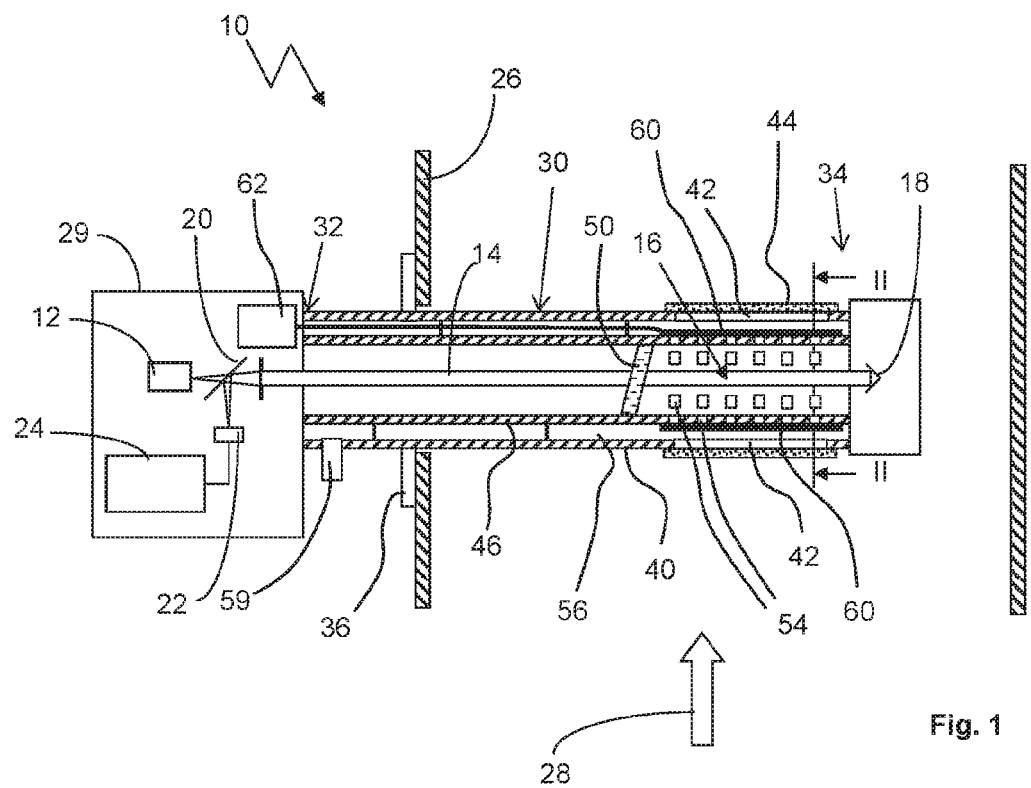

(51) Int. Cl.
  *G01N 33/00* (2006.01)
  *F16K 7/07* (2006.01)
  *G01N 21/3504* (2014.01)
  *G01N 1/22* (2006.01)
  *G01N 21/27* (2006.01)
  *G01N 21/53* (2006.01)

(52) U.S. Cl.
  CPC ......... *G01N 1/2247* (2013.01); *G01N 21/276* (2013.01); *G01N 21/31* (2013.01); *G01N 21/3504* (2013.01); *G01N 21/534* (2013.01); *G01N 33/0006* (2013.01); *G01N 33/0044* (2013.01); *G01N 2001/4088* (2013.01); *G01N 2021/536* (2013.01)

(56) References Cited

OTHER PUBLICATIONS

"Dichtung (Technik)—Wikipedia", Sep. 20, 2015 (Sep. 20, 2015), XP055297124.

\* cited by examiner

APPARATUS FOR OPTICAL IN-SITU GAS ANALYSIS

The invention relates to an apparatus for optical in-situ gas analysis, the apparatus comprising a housing; a measuring lance whose one first end is connected to the housing and whose other second end projects into the gas to be measured; a light transmitter that is arranged in the housing and whose light is conducted into the measuring lance and is reflected by a reflector arranged at the second end onto a light receiver, with the optical path defining an optical measurement path within the measuring lance; and an evaluation device for evaluating received light signals of the light receiver.

Specific gas portions, e.g. hydrogen sulfide, carbon monoxide, SO2, NH3, NO, NO2, HCl, HF or the like, are measured by means of optical transmission or light scattering using such apparatus. The concentration of these gas portions is typically determined in this respect.

Fields of application are, for example, emission measurements of industrial plant in which the exhaust gases in an exhaust gas passage have to be monitored with respect to their content of specific molecular compounds. The gas flows to which the optoelectronic apparatus is exposed to measure the desired gas portions are frequently characterized by high particulate loads such as smoke, dusts or other aerosols. These high particulate loads cause high light absorption and/or high light scattering that greatly impairs/impair the actual measurement and even makes/make it impossible. Hydrogen sulfide, for example, has a very wide absorption and also ultrafine dust. It is then no longer possible to distinguish whether the absorption is due to the hydrogen sulfide or to the dust.

It is known (e.g. U.S. Pat. No. 4,549,080) to provide filters that comprise a piece of tube of porous material in whose interior the measurement path is located to keep out such particulates. Due to the porous structure, the gas to be measured can admittedly move into the measurement path; however, particulates such as smoke, dusts or aerosols can also be kept away depending on the pore size.

It is disadvantageous here that such in-situ devices have to tested, inspected and calibrated from time to time and that a test gas has to be introduced into the measurement path for this purpose. The test gas is blown into the measurement path for this purpose. The measurement path is, however, not hermetically sealed, but the test gas rather escapes through the pores of the filter into the exhaust gas passage. A sufficient quantity of test gas therefore has to be permanently blown at a sufficient pressure into the measurement path for the duration of the calibration measurements. The test gas quantity required for a calibration is correspondingly high, which causes correspondingly high costs. This disadvantage becomes particularly noticeable with long measurement paths with a correspondingly long, porous filter.

Starting from this prior art, it is the object of the invention to provide an improved apparatus with which the consumption of test gas can be reduced.

This object is satisfied by an apparatus having the features of claim 1.

The apparatus in accordance with the invention for optical in-situ gas analysis comprises
  a housing;
  a measuring lance whose one first end is connected to the housing and whose other second end projects into the gas to be measured;
  a light transmitter that is arranged in the housing and whose light is conducted into the measuring lance and is reflected by a reflector arranged at the second end onto a light receiver, and the optical path defines an optical measurement path within the measuring lance; and an evaluation device for evaluating received light signals of the light receiver.

In accordance with the invention, the measuring lance has an outer tube, with the outer tube having openings for the gas to be measured. The openings can be closed by at least one seal for the test phase, with the seal searingly closing the openings by the enlargement of its volume.

The openings toward the measurement path are closed in a simple manner by the quasi "inflatable" seal so that measuring gas can no longer enter into the measurement path. The measurement path can then be flooded with test gas. A defined leak via a discharge valve or a defined leak that can, however, be small, is sensible in this respect to displace the measuring gas still present after the closing of the openings out of the measurement path by the test gas. The test gas can, however, only escape through the small defined leak and no longer through the filter. A test gas filling of the measurement path is achieved by a small excess pressure in the arising measurement chamber in connection with a constant test gas flow. The test gas consumption thus becomes calculable and can be considerably minimized and is also very largely independent of the length of the active measurement path. The measurement path is furthermore evenly filled with test gas. The test gas consumption is constant and predictable.

Such seals are simple to handle, do not effect any mechanical wear and independently adapt to different geometries in the lance.

These seals also open up the possibility of effecting a "breathing effect" by periodic or pulsating volume changes so that a better gas exchange between the measurement path and the exhaust gas passage takes place during the normal measurement phase.

The seals of the apparatus in accordance with the invention do not require any classically moved parts, whereby less wear and a high service life results. Only a few components are required. The seal is very simple from a construction aspect and large opening surfaces are possible that allow a better gas exchange. A large tolerance compensation is possible by the expansion-capable seal.

The test operation could be carried out automatically in defined time intervals or by a manual actuation. This would be reflected in variants of the apparatus in accordance with the invention graded in price.

In an embodiment of the invention, a volume change takes place using pneumatic or hydraulic means, for example by means of an associated pump.

In order to keep particulates such as smoke, dusts or aerosols out of the measurement path in a known manner during the measurement, a gas-permeable filter is provided through which the measuring gas enters into the measurement path. The filter, for example, comprises a tube piece of porous material and is held by a suitable support construction. The measurement path is located in the interior of the measurement path. Due to the porous structure, the gas to be measured can admittedly move into the measurement path; however, particulates can be kept away depending on the pore size.

A test gas connection is provided at the measuring lance or at the housing in a further development in order to be able to fill the measurement path with a test gas via it. In an embodiment of the invention, the test gas could simultaneously be used as a blowing gas for the seals.

A heating coil contacting the outer tube at the outside can prevent the ingress of water in applications in a wet measuring gas.

Figure 2:
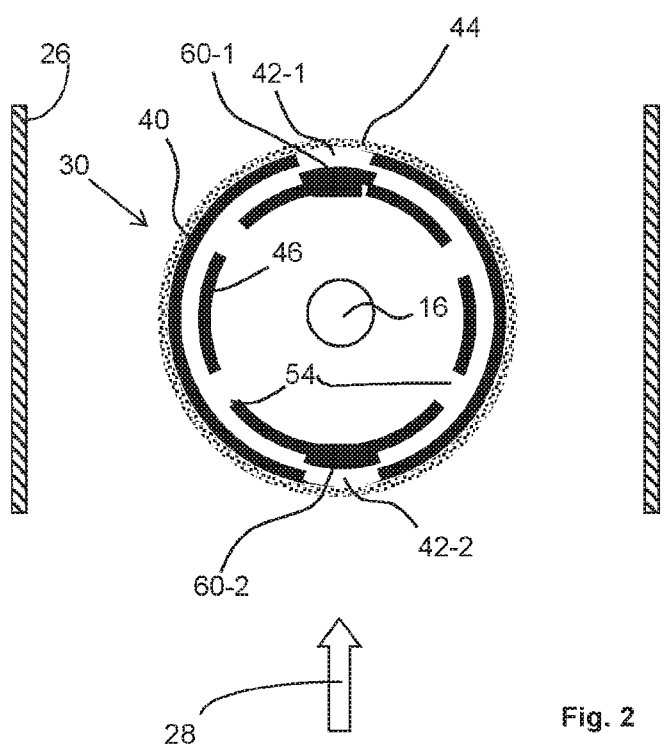
Figure 3:
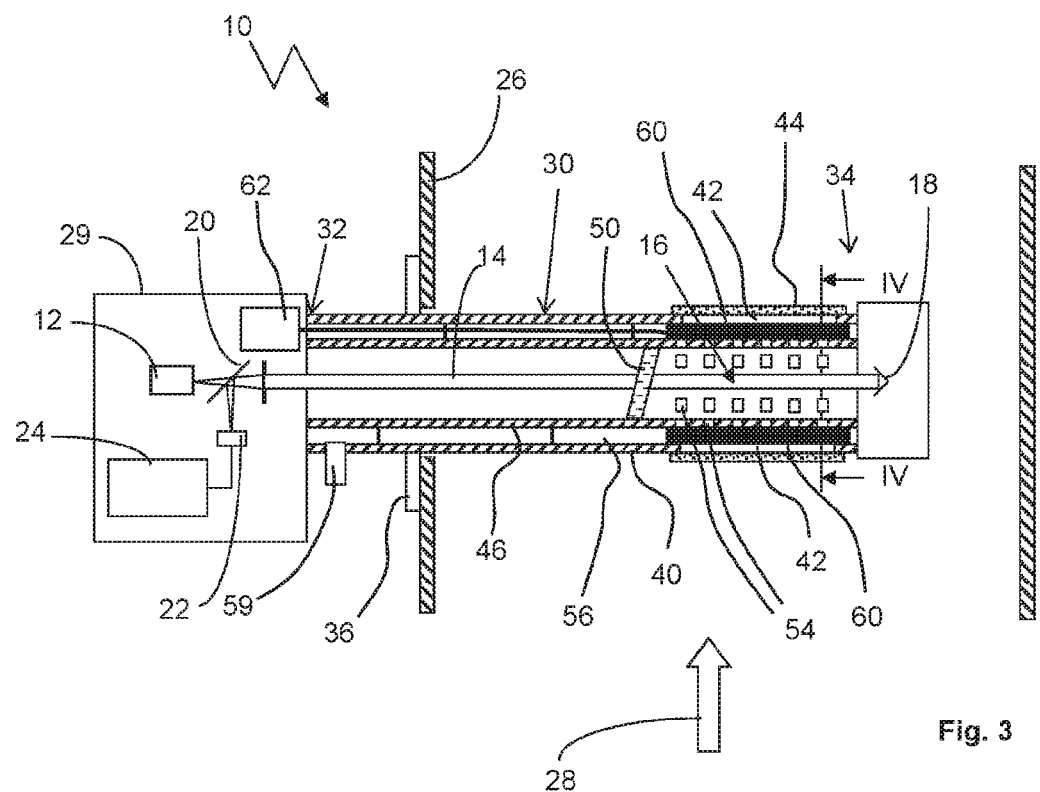
Figure 4:
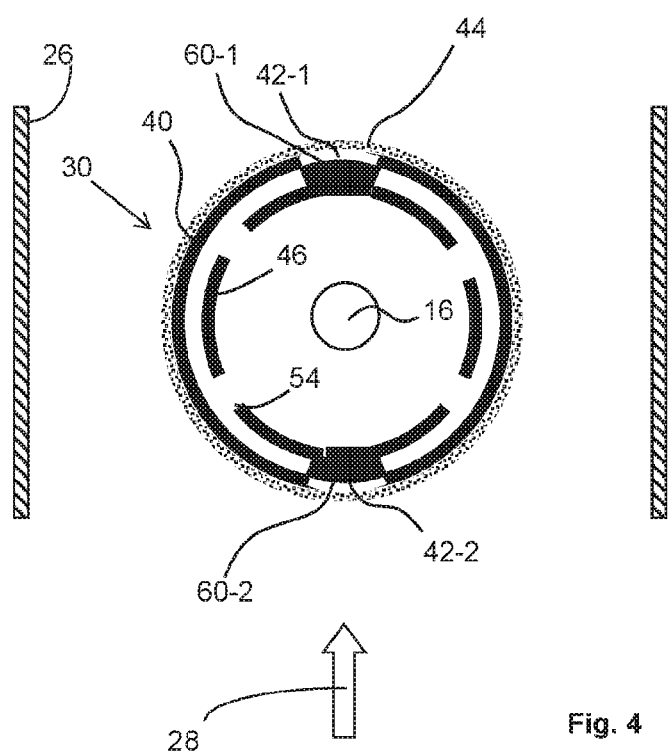
Figure 5:
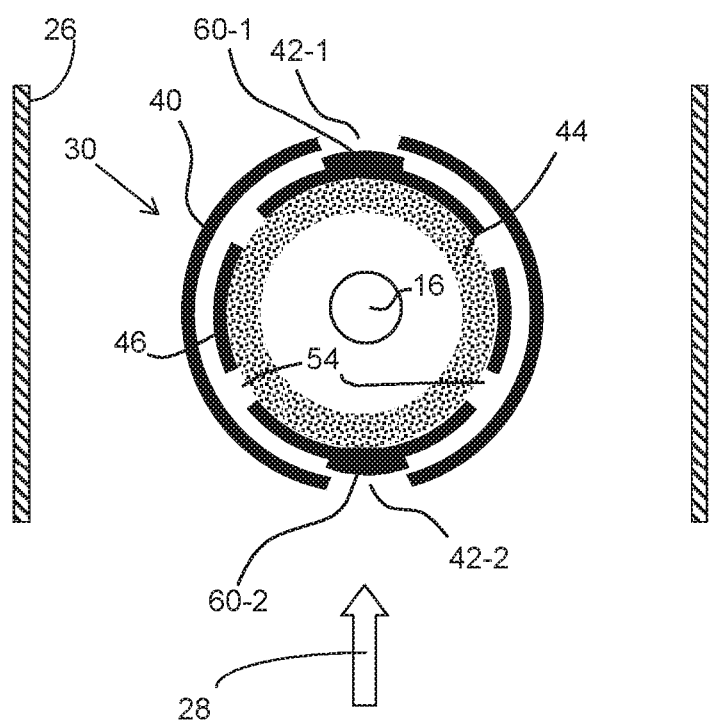
Figure 6:
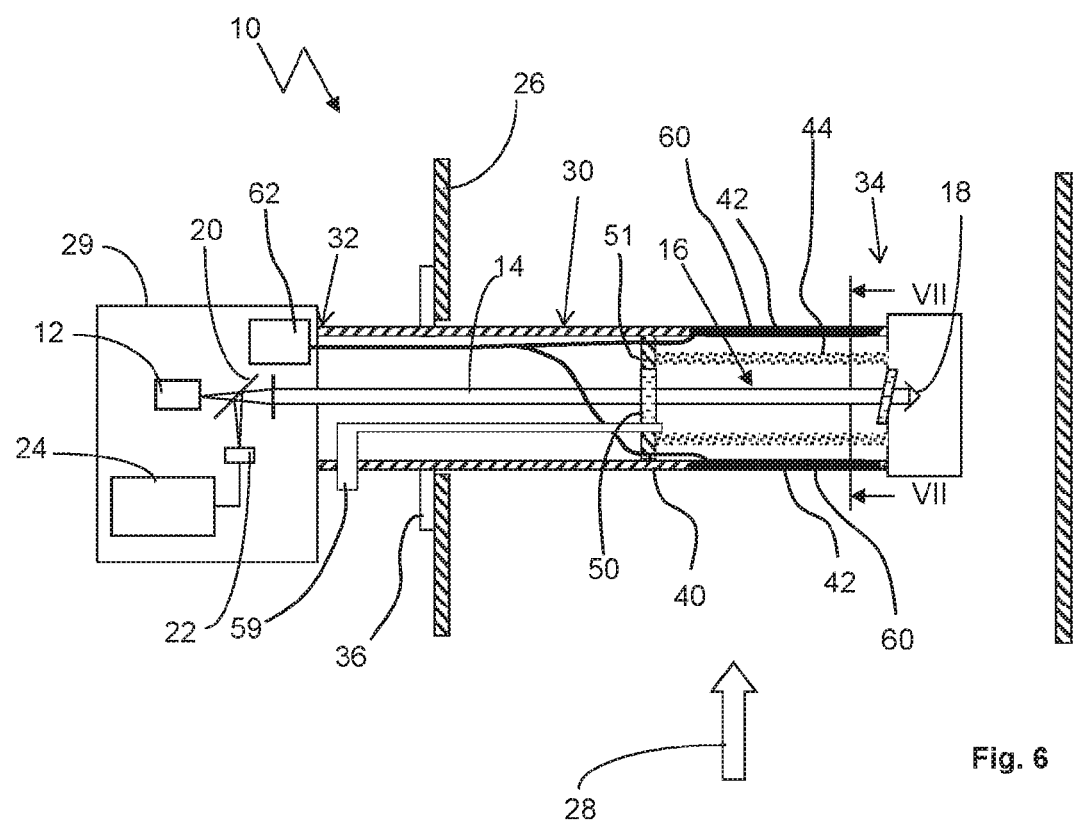

The invention will be explained in detail in the following with reference to embodiments and to the drawing. There are shown in the drawing:

FIG. 1 a schematic representation of an embodiment of the apparatus for optical in-situ gas analysis in a gas flow;

FIG. 2 the apparatus of FIG. 1 in a section along the line II-II;

FIG. 3 the apparatus of FIG. 1 with closed openings;

FIG. 4 the apparatus of FIG. 2 in a section along the line IV-IV;

FIG. 5 an alternative embodiment with an inwardly disposed filter,

FIG. 6 a view as FIG. 1 of a further embodiment; and

Figure 7:
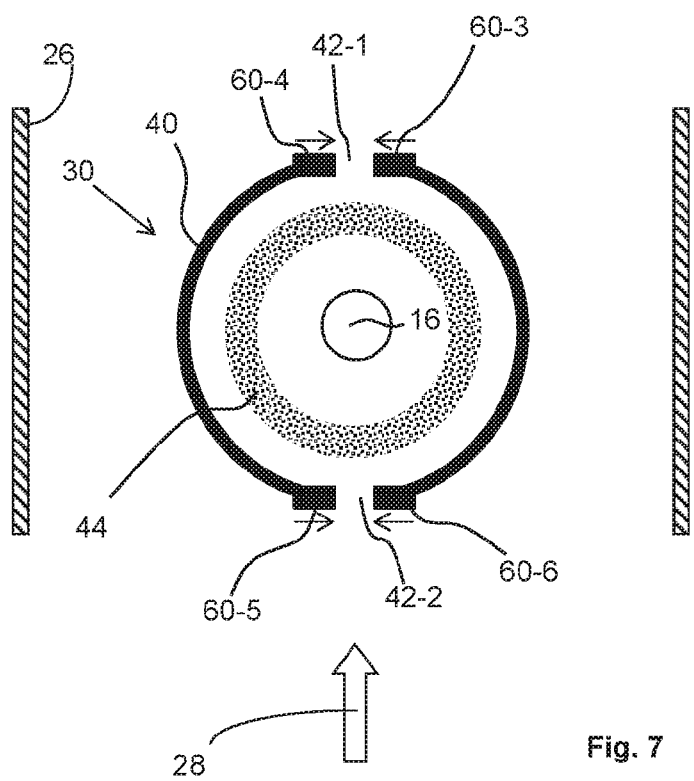

FIG. 7 the apparatus of FIG. 6 in a section along the line VII-VII.

An optoelectronic apparatus 10 in accordance with the invention for optical in-situ gas analysis of a gas flow 28 that is conducted in an exhaust gas passage 26 has a light transmitter 12 that transmits a transmitted light beam 14 in a first embodiment shown in FIG. 1. The transmitted light beam 14 defines a measurement path 16 and is received by a light receiver 22 after reflection at a retroreflector 18 and at a beam splitter 20. The light receiver 22 generates received signals in dependence on the incident light that are evaluated in an evaluation device 24, for example to determine the concentration of a component of the measuring gas.

Such an optoelectronic apparatus 10 is configured in this embodiment as a transmissiometer such that the intensity of the light radiating through the measurement path 16 is measured by the light receiver 22. As a rule, the light transmitter 12 is tuned to a specific wavelength which is absorbed by a gas proportion to be inspected, for example hydrogen sulfide. A statement can then be made via the light received at the light receiver 22 as to how high the concentration of the gas proportion of interest is in the gas flow 28 which is conducted in the exhaust gas passage 26.

The optoelectronic apparatus 10 comprises a housing 29 having a measuring lance 30 whose one first end 32 is connected to the housing 29 and whose other second end 34 projects into the exhaust gas passage 26 and thus into the gas 28 to be measured. The housing 29 and the measuring lance 30 are fixed to a wall of the exhaust gas passage via a fastening flange 36.

The optoelectronic units such as the light transmitter 12, light receiver 22 and evaluation device 24 are arranged in the housing 29 and the light is conducted through the measurement path 16 in the measuring lance 30. The retroreflector 18 is held in a reflector housing at the second end 34 of the measuring lance 30.

The measuring lance 30 has an outer tube 40 that extends over the total length of the measuring lance 30 and is fixed at its one end to the housing 29 and holds the retroreflector at its other end. The outer tube 40 has openings 42 in the region of the outer tube 40 that projects into the exhaust gas passage 26 such that portions of the gas flow 28 can move into the measurement path 16.

The gas flow 28 that is conducted in the exhaust gas passage 26 and that is only indicated by an arrow 28 can be loaded with particulates, for example dust, smoke or other aerosols, with the particulates disturbing the actual optical measurement over the measurement path 16. To keep the particulates out of the measurement path 16, a gas-permeable filter 44, preferably of porous material, is provided at least in the region of the openings 42. In the embodiment in accordance with FIGS. 1 and 2, the filter 44 is located at the outer side of the outer tube 40.

The measuring lance 30 furthermore has an inner tube 46 that is preferably arranged coaxially to the outer tube 40 in this first embodiment. The inner tube 46 has the same length as the outer tube 40. The light beam 14 is conducted in the inner tube 46. The interior of the inner tube 46 is divided into two parts by a sealing window 50. No measuring gas and thus no pollutants from the second part facing the reflector 18 can enter in the first part that faces the housing 29. In the second part, that is located at the end of the inner tube 46 at the reflector side, the inner tube 46 has openings 54 through which the measuring gas 28 can move into the measurement path 16.

The openings 42 in the outer tube 40 in this embodiment are configured as two larger slit openings 42-1 and 42-2 (FIG. 2) through which the measuring gas 28 can enter and leave the filter 44. The measuring gas 28 can then move up to and into the measurement path 16 through the openings 54 in the inner tube 46.

The two openings 42-1 or 42.-2 of the outer tube 40 can be closed in accordance with the invention by a respective one seal 60-1 or 60-2 (in the following also simply called "seal 60". The seal 60 comprises a strip of elastic material that is adapted in shape to the elongate opening 42, with the volume of the strip being variable. This volume change can take place pneumatically or hydraulically or in a comparable manner and can be driven by a corresponding actuator 62, for example a pump.

In an operating position in which the regular measurement can be carried out and in which measuring gas 28 can enter into the measurement path 16 (working operation), the seals 60 are in the non-expanded state and release the openings 42 or 42-1 and 42-2. This is shown in FIGS. 1 and 2.

In a test operation in which no measuring gas may enter into the measurement path and the measurement path 16 has to be kept free of measuring gas so that a test operation can take place, the seals 60 are in the expanded state and close the openings 42 or 42-1, 42-2. This is shown in FIGS. 3 and 4.

To have the measurement path 16 free of measuring gas after closing the openings 42, a test gas connection 59 is provided via which test gas can be conducted into the outer tube and inner tube such that the remaining measuring gas can be displaced from the measurement path 16. It is necessary for a displacement that so much test gas is filled in that the pressure in the measurement path 16 is slightly higher than in the exhaust gas passage 26. At the same time, a defined leak is provided such that measuring gas is "flushed" from the inner tube and the outer tube and thus from the measurement path 16.

Further construction alternatives are possible without departing from the basic idea of the invention, namely the closing of the openings 42 by volume-variable seals 60. Examples of alternative constructions are shown in FIGS. 5 to 7 and are briefly described in the following. In this respect, the same parts as in the first embodiment have the same reference numerals are not described again.

FIG. 5 shows a very similar embodiment to that of FIGS. 1 to 4, with here the modification only comprising the filter 44 still being arranged within the inner tube 46.

A further embodiment is shown in FIGS. 6 and 7. There is no inner tube there, but rather only the outer tube 40 whose tube cross-section can in principle be as desired, e.g. round, polygonal, oval or the like. The measurement path 16 lies in the interior of the filter 44 that is held in a suitable manner in the outer tube 40. This is done here in that the filter 44 is held at the front face, on the one hand, by a wall 51 in which the window 50 is arranged and, on the other hand, by the reflector housing. It is also ensured in this manner that the measuring gas can only enter into the measurement path through the filter 44.

The seals 60 are now, as can be recognized in the cross-section of FIG. 7, arranged at the outer tube 40 at the longitudinal sides of the openings 42-1 and 42-2. Two seals 60-3 and 60-4 or 60-5 and 60-6 are provided for each opening in this example that increase volume-wise in the direction of the arrow in each case to close the opening 42-1 or 42-2. The seals 60-3 and 60-4 or 60-5 and 60-6 can again be controlled via the actuator 62.

When the openings 42-1 and 42-2 are closed, test gas can be introduced into the measurement volume via the test gas connection 59, that is extended up to and into the interior of the filter 44 in this embodiment, and can displace the measuring gas out of the measurement path 16.

Further construction alternatives are conceivable. The filter and the measurement path e.g. do not necessarily have to be coaxial to the outer tube. They could also be eccentric. As mentioned, the outer tube also does not have to be round in cross-section. It primarily serves as a support construction for the reflector housing, the filter and the measurement path and as a separating medium with respect to the gas flow 28 in the exhaust gas passage 26.

The invention claimed is:

1. An apparatus for optical in-situ gas analysis, comprising
   a housing;
   a measuring lance having a first end and a second end, with the first end being connected to the housing, with the second end projecting into the gas to be measured and with the measuring lance having an optical path;
   a light transmitter that is arranged in the housing and with the light from the light transmitter being conducted into the measuring lance;
   a light receiver which receives light reflected by a reflector arranged at the second end, with the optical path defining an optical measurement path within the measuring lance;
   an evaluation device for evaluating received light signals of the light receiver; and
   a test gas connection via which test gas can be conducted into the measurement path,
   wherein the measuring lance has an outer tube and the outer tube has openings for the gas to be measured; wherein the openings can be closed by at least one seal and with the at least one seal sealingly closing the openings by enlarging its volume.

2. The apparatus in accordance with claim 1, wherein the apparatus is configured to bring about the enlargement of the volume of the at least one seal by using pneumatic or hydraulic means.

3. The apparatus in accordance with claim 1, wherein an inner tube is arranged in the outer tube.

4. The apparatus in accordance with claim 1, further comprising a gas-permeable filter that is arranged in or at the measuring lance, with the measuring gas entering into the measurement path via the gas-permeable filter.

* * * * *